United States Patent [19]

Baquero et al.

[11] Patent Number: 5,389,513
[45] Date of Patent: Feb. 14, 1995

[54] **METHOD FOR DETECTING *LISTERIA MONOCYTOGENES***

[75] Inventors: Fernando Baquero, Madrid, Spain; Pascale Cossart, Paris, France

[73] Assignee: Institut Pasteur, Paris, France

[21] Appl. No.: 688,826

[22] Filed: Apr. 22, 1991

Related U.S. Application Data

[63] Continuation of Ser. No. 227,402, Aug. 2, 1988, abandoned, which is a continuation of Ser. No. 143,490, Jan. 13, 1988, abandoned.

[51] Int. Cl.$^6$ .................... C12Q 1/68; C07H 21/04
[52] U.S. Cl. ..................................... 435/6; 536/24.32
[58] Field of Search .................... 435/6; 536/27, 24.32

[56] References Cited

U.S. PATENT DOCUMENTS 4,358,535  11/1982  Falkow et al. ....................... 435/6

OTHER PUBLICATIONS

Vicente et al Ann Inst Pasteur Microbiol 138(3):385–87 (1987).
Vicente et al Ann Inst Pasteur Microbiol 138(2):250–51 (1987).
Mengaud et al. Infect & Immunity 55(12): 3225–27 (1987).
Kathariou et al Ann Inst Pasteur/3rd Forum in Microbiol 138(2): 256–58 (1987).
Kathariou et al. Infection & Immunity 56(2):534–36 (1988).
Mengaud et al Infection & Immunity 56(4):766–72 (1988).
Rocourt et al. Int. Journal of Systematic Bacteriology 37(3):298–300 (1987).
Vicente et al. FEMS Microbiol Letters 30:77–79 (1985).
Hames et al Nucleic Acids Hybrid IRL Press Wash DC 1985 pp. 17–111.
Suggs et al Proc Natl. Acad Sci 78(11):6613–17 (1981).
Datta et al. App Envion Microbio 53(9):2256–59 (1987).
Gaillard et al. Infection & Immunity, 52(1):50–55 (1986).
Cossort et al Infection 16 (suppl 2):S157–59 (1988).
Kathariou et al Journal of Bacteriol 169(3) 1291–97 (1987).
Kathariou et al., Ann. Inst. Pasteur/Microbiol., 183(2):256–258 (1987).
Datta et al., J. Assoc. Anal. Chem., 71(3):673–675 (1988).

*Primary Examiner*—Mindy B. Fleisher
*Attorney, Agent, or Firm*—Finnegan, Henderson, Farabow, Garrett & Dunner

[57] ABSTRACT

A DNA probe is disclosed which is capable of hybridizing to a portion of the genome of pathogenic *Listeria monocytogenes* but which does not hybridize to portions of the genomes of other *Listeria* species and other humilytic bacteria. This probe is useful to identify food sources infected with *Listeria monocytogenes* and to distinguish these food services from those infected nearly with non-pathogenic *Listeria* species. In addition, methods for the detection of pathogenic *Listeria* in samples using the disclosed probes are provided.

12 Claims, 5 Drawing Sheets

| FIRST nt. | 10 | 20 | 30 | 40 | 50 | 60 | 70 | 80 | 90 | 100 |
|---|---|---|---|---|---|---|---|---|---|---|
| +1 | GGATCCGATA<br>CCTAGGCTAT | ATCAAAACTA<br>TAGTTTTGAT | TCGTTGCTGT<br>AGCAACGACA | TTTGCTCGTC<br>AAACGAGCAG | TTTTAAACGC<br>AAAATTTGCG | ATAATAATGG<br>TATTATTACC | TTTCTTTTGG<br>AAAGAAAACC | ATTTTCTTT<br>TAAAAGAAA | AAAAATTGAG<br>TTTTTAACTC | TAATCGTTTC<br>ATTAGCAAAG |
| +101 | TAATACACCT<br>ATTATGTGGA | GAAAGTGATG<br>CTTTCACTAC | CATTTAAAAA<br>GTAAATTTTT | AATTGGCCCA<br>TTAACCGGGT | TGGTAAATGT<br>ACCATTTACA | TGAGATTGTC<br>ACTCTAACAG | TTTGCTCTA<br>AAACGAGAT | ATATCGATGT<br>TATAGCTACA | ACCGTATTCC<br>TGGCATAAGG | TGCTTCTAGT<br>ACGAAGATCA |
| +201 | TGTTGGTACA<br>ACAACCATGT | ATGACATCGT<br>TACTGTAGCA | TTGTGTTTGA<br>AACACAAACT | GCTAGTGGTT<br>CGATCACCAA | TGGTTAATGT<br>ACCAATTACA | CCATGTTATG<br>GGTACAATAC | TCTCCGTTAT<br>AGAGGCAATA | AGCTCATCGT<br>TCGAGTAGCA | ATCATGTGTA<br>TAGTACACAT | CCTGGTATAG<br>GGACCATATC |
| +301 | AGAGCGCTGC<br>TCTCGCGACG | TAGGTTTGTT<br>ATCCAAACAA | GTGTCAGGTA<br>CACAGTCCAT | GAGCGGACAT<br>CTCGCCTGTA | CCATTGTTT<br>GGTAACAAA | GTAGTTACAG<br>CATCAATGTC | AGTTCTTTAT<br>TCAAGAAATA | TGGCTTATTC<br>ACCGAATAAG | CAGTTATTAA<br>GTCAATAATT | GCGAATATGC<br>CGCTTATACG |
| +401 | TTTTCCGCCT<br>AAAGGCGGA | AATGGAAAG<br>TTACCCTTTC | TAAAAAGTA<br>ATTTTTTCAT | TTATGTTGAG<br>AATACAACTC | CAGAGTAATA<br>GTCTCATTAT | AAACTAATGT<br>TTTGATTACA | GCGTTGCAAA<br>CGCAACGTTT | TAATTCTTAT<br>ATTAAGAATA | ACAAAATGGC<br>TGTTTTACCG | CCCCTCCTTT<br>GGGGAGGAAA |
| +501 | GATTAGTATA<br>CTAATCATAT | TTCCTATCTT<br>AAGGATAGAA | AAAGTGACTT<br>TTTCACTGAA | TTATGTTGAG<br>AATACAACTC | GCATTAACAT<br>CGTAATTGTA | TTGTTAACGA<br>AACAATTGCT | GGGTTGCAAA<br>CCGAACGTTT | TAGAATAAAG<br>ATCTTATTTC | TATAAGCA<br>GATATTTCGT |
| +601 | AGCATATAAT<br>TCGTATATTA | ATTGCGTTTC<br>TAACGCAAAG | ATCTTTAGAA<br>TAGAAATCTT | GCGAATTTCG<br>CGCTTAAAGC | CCAATATAT<br>GGTTATATA | AATTATCAAA<br>TTAATAGTTT | CGATAAGGG<br>GCTATTTCCC | ACAGCAGGAC<br>TGTCGTCCTG | AGAGAGGGGT<br>TCTCTCCCCA | ATTGGCATT<br>TAACCGTAA |
| +701 | AAAATGTAGA<br>TTTTACATCT | AGGAGAGTGA<br>TCCTCTCACT | AACCCATGAA<br>TTGGGTACTT | AAAAATAATG<br>TTTTTATTAC | CTAGTTTTA<br>GATCAAAAT | TTACACTTAT<br>AATGTGAATA | ATTAGTTAGT<br>TAATCAATCA | GGCAAACGGT<br>CCGTTTGCCA | CGCAACAAAC<br>GCGTTGTTTG | ATTAGGTTAA<br>TAATCCAATT |
| +801 | GATGCATCTG<br>CTACGTAGAC | CATTCAATAA<br>GTAAGTTATT | AGAAAATTCA<br>TCTTTTAAGT | ATTTCATCCA<br>TAAAGTAGGT | TGGCACCACC<br>ACCGTGGTGG | AGCATCTCCG<br>TCGTAGAGGC | CCTGCAAGTC<br>GGACGTTCAG | CTAACAATTG<br>GATTGTTAAC | CGCAACGCC<br>GCGTTGCGG | TGAAGCAAAG<br>ACTTCGTTTC |
| +901 | ATGAAATCGA<br>TACTTTAGCT | TAAGTATATA<br>ATTCATATAT | CAAGGATTGG<br>GTTCCTAACC | ATTACAATAA<br>TAATGTTATT | AAACAATGTA<br>TTTGTTACAT | TTAGTATACC<br>AATCATATGG | ACGGAGATGC<br>TGCCTCTACG | AGTGACAAAT<br>TCACTGTTTA | GTGCCGCCAA<br>CACGGCGGTT | AAACACGCGG<br>TTTGTGCGCC |
| +1001 | CAAAGATGGA<br>GTTTCTACCT | AATGAATATA<br>TTACTTATAT | TIGTGTGGA<br>AACAACACCT | GAAAAGAAG<br>CTTTTTCTTC | AAATCCATCA<br>TTTAGGTAGT | ATCAAAATAA<br>TAGTTTTATT | TGCAGACATT<br>ACGTCTGTAA | CAAGTTGTGA<br>GTTCAACACT | ATGCAATTC<br>TACGTTAAAG | GAGGCTAACC<br>CTCCGATTGG |

```
+2301  AATCCAATCG AATAATTGTA AAAGTAATAA AAAATTAAGA ATAAACCGC  TTAACACACA CGAAAAATA  AGCTTGTTTT GCACTCTTCG TAAATTATTT
       TTAGGTTAGC TTATTAACAT TTTCATTATT TTTTAATTCT TATTTGGCG  AATTGTGTGT GCTTTTTAT  TCGAACAAAA CGTGAGAAGC ATTTAATAAA

+2401  TGTGAAGAAT GTAGAACAG  GCTTATTTT  TAATTTTTT  AGAAGAATTA ACAAATGTAA AAGATATCT  GACTGTTAT  CCATATAATA TAAGCATATC
       ACACTTCTTA CATCTTTGTC CGAATAATAA ATTAAAAAAA TCTTCTTAAT TGTTTACATT TTCTTATAGA CTGACAAATA GGTATATTAT ATTCGTATAG

+2501  CCAAAGTTTA AGCCACCTAT AGTTCTACT  GCAAAACGTA TAATTTAGTT CCCACATATA CTAAAAACG  TGTCCTTAAC TCTCTCTGTC AGATTAGTTG
       GGTTTCAAAT TCGGTGGATA TCAAAGATGA CGTTTTGCAT ATTAAATCAA GGGTGTATAT GATTTTTGC  ACAGGAATTG AGAGAGACAG TCTAATCAAC

+2601  TAGGTGGCTT AAACTTAGTT TTACGAATTA AAAAGGAGCG GTGAAATGAA AAGTAAACTT ATTTGTATCA TCATGGTAAT AGCTTTTCAG GCTCATTTCA
       ATCCACCGAA TTTGAATCAA AATGCTTAAT TTTCCCTCGC CACTTTACTT TTCATTTGAA TAAACATAGT AGTACCATTA TCGAAAAGTC CGAGTAAAGT

+2701  CTATGACGGT AAAGCAGAT  TCTGTCGGGG AAGAAAAACT TCAAATAAT  ACACAAGCCA AAAAGACCCC TGCTGATTTA AAAGCTTGC  CAGATTCCTG
       GATACTGCCA TTTCGTCTA  AGACAGCCCC TTCTTTTTGA AGTTTTATTA TGTGTTCGGT TTTTCTGGGG ACGACTAAAT TTTCGAACG  GTCTAAGGAC
```

FIG. 2C 5,389,513

METHOD FOR DETECTING *LISTERIA MONOCYTOGENES*

This is a continuation of application Ser. No. 07/227,402, filed Aug. 2, 1988, now abandoned which is a continuation of application Ser. No. 07/143,490, filed Jan. 13, 1988, now abandoned.

BACKGROUND OF THE INVENTION

*Listeria monocytogenes* is a facultative intracellular gram positive bacterium. In the genus Listeria, only *L. monocytogenes* and *L. ivanovii* are pathogens for human and animals. *L. monocytogenes* is increasingly recognized as responsible for severe infections in both animals and humans. Pregnant women, new-born and immunocompromised patients are especially susceptible to infection.

To avoid human infection, food sources have, routinely been screened for the presence of *Listeria* organisms. Potential food sources infected with any species of *Listeria* have routinely been discarded to avoid infecting the consumer because of the time and expense involved in determining whether the infecting organisms are or are not pathogenic. Thus, there is a need for a means identifying and distinguishing pathogenic *Listeria*.

In addition, another need has arisen for means to distinguish readily and efficiently between pathogenic and non-pathogenic Listeria species. This information is necessary to determine the course of treatment of suspected listeria infections and for the development of data for epidemiological studies.

The present inventors have developed a DNA probe capable of distinguishing pathogenic *Listeria* species from non-pathogenic *Listeria* species. These probes and their uses are described more fully below.

BRIEF DESCRIPTION OF THE DRAWINGS

FIGS. 2-1, 2-2, and 2-3 depicts the nucleotide sequence of the hlyA gene and its proximal region.

FIG. 3 depicts the schematic comparison of the amino-acid sequences of listeriolysin O (LLO), streptolysin (SLO) and pneumolysin (PLY): sequences, represented by lines, are aligned on the unique cysteine (C) in the monologous position. Signal sequences are indicated by thick lines. ($\Delta$) indicates deletions of one amino acid, and the numbers, the coordinates in the protein sequence.

DETAILED DESCRIPTION OF THE PREFERRED EMBODIMENTS

Figure 1:
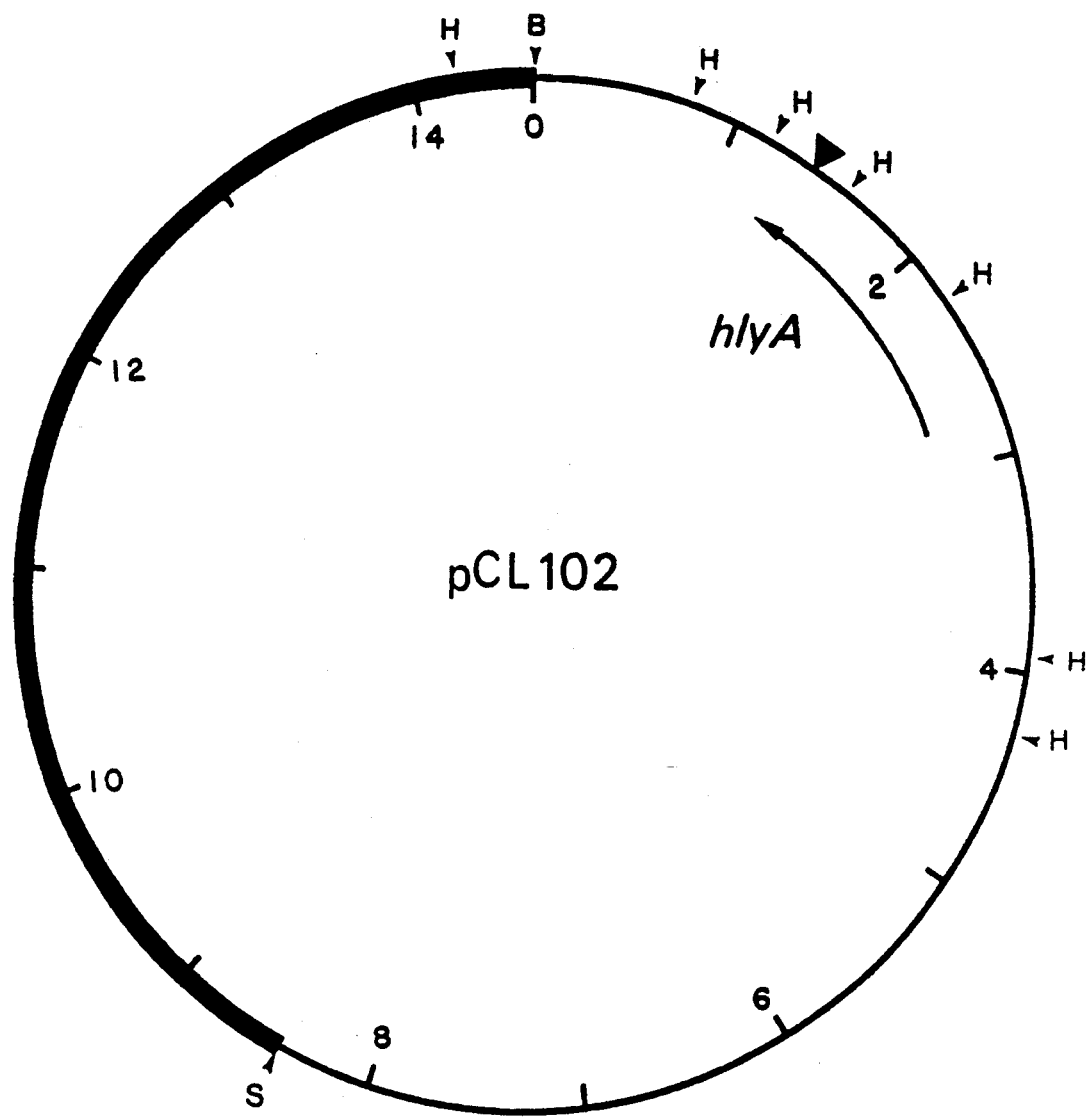
FIG. 1 is a restriction map of plasmid pCL loz. The restriction site BamHI is indicated by "B"; SalI by "S"; and HindIII by "H". The inverted triangle corresponds to the insertion site of transposon Tr1545.
Figure 3:
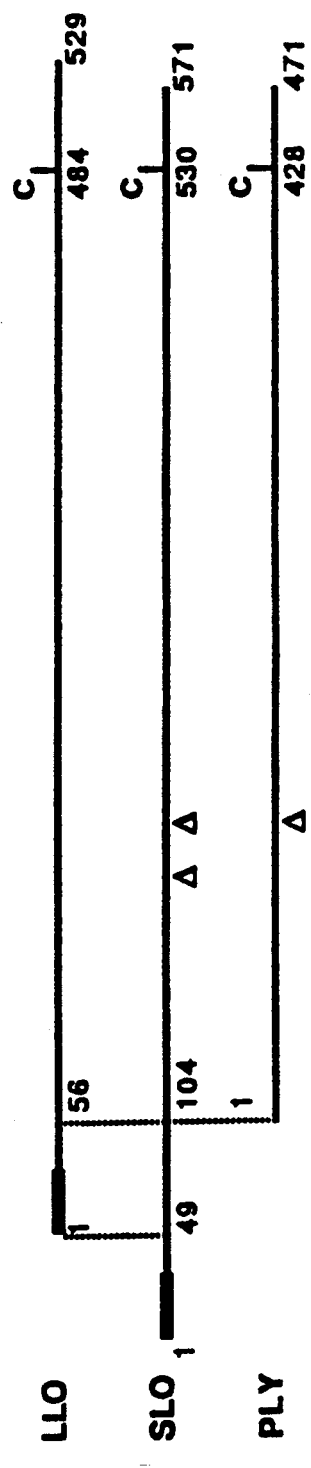

Among the virulence factors which enable *Listeria* organism to enter, survive and grow within cells, including macrophages, the SH-activated hemolysin is a serious candidate. The first observation which suggested a correlation between hemolysin and viruleace was that all non-hemolytic listeria strains are experimentally non-pathogenic and that all pathogenic strains of *Listeria* produce zones of hemolysis on blood agar plates. Hemolysin production being a phenotype easily identified on blood agar plates, genetic studies were undertaken and transposon mutagenesis was performed to obtain a non hemolytic (Hly$^-$) mutant. This mutant was avirulent; insertion of a single copy of the transposon had inactivated the hemolytic phenotype. Spontaneous loss of the transposon led to the recovery of the Hly$^+$phenotype and virulence. It was further shown that the Hly$^-$mutant, although phagocytosed at the same rate as that of the themolytic revertant strain, stayed in the phagolysosome and failed to replicate significantly within the human enterocyte-like cell line Cado-2. Electron microscopic study demonstrated that bacteria from the Hly$^-$mutant remained inside the phagosomes during cellular infection, whereas hemolytic bacteria from *L. monocytogene* became free in the cytoplasm. These data were a strong indication that disruption of vacuole membranes by hemolysin-producing strains of *L. monocytogenes* might be a key mechanism allowing bacteria to escape from phagosome and to multiply within the cell cytoplasm.

The SH-activated hemolysin referred to herein as "Listeriolysin O" has been purified from *L. monocytogenes* culture supernatants. It shares the typical properties of other bacterial sulfhydryl-activated toxins: (i) inhibition with very low amounts of cholesterol, (ii) activation by reducing agents and suppression of the lyric activity by oxidation, (iii) cross-reactivity with streptolysin O. Antiserum raised against the purified protein allowed the demonstration that the Hly$^-$mutant produced a truncated protein, indicating that the transposon had inserted in the listeriolysin O structural gene. Accordingly the region of insertion of the transposon was cloned and sequence analysis showed that it had inserted in an open reading frame (ORF). The deduced sequence of this ORF shared homologies with streptolysin O and pneumolysin. From this, the identity of the locus of insertion of the transposon in the listeriolysin O gene, called hlyA has been determined.

In order to elucidate the role of listeriolysin O in pathogenicity, and to clarify the conflicting views on the nature and the number of *Listeria* hemolysin(s) a structural and functional analysis of the chromosomal region carrying hlyA was undertaken. In the Examples which follow, the complete nucleotide sequence of hlyA and an extensive analysis of the deduced protein sequence, especially a comparison with other membrane-damaging thiol-activated hemolysins is set forth. In addition, DNA—DNA hybridization studies which indicate that the disclosed probes are present only in *Listeria monocytogenes* are provided.

These analyses lead to the identification of the DNA sequence of a 2.8 kb portion of the *Listeria monocytogenes* genome. From this piece of chromosomal DNA, hlyA has been identified. Within this gene, a 651 bp HindIII fragment (oligo 1309–1965) is preferred for use as a probe. In addition, certain smaller oligos are contemplated for use as probes. Preferably, oligo 1775–1805 would make a suitable probe. In addition, oligos 1412–1441; 1643–1665; and 1810–1835 are contemplated for use as probes.

As one of ordinary skill in the art will note, the desired characteristics of these probes include their ability to hybridize with *Listeria monocytogenes* DNA while not hybridizing with DNA from other *Listeria* species. In addition, it is a preferred characteristic of these probes that they do not cross react with DNA from other hemolytic bacterial species such as *Streptococcus*.

In addition to the probes discussed above, various improved probes are contemplated. In these probes, certain modifications are made which will not affect their ability to hybridize with the target DNA but will increase the strength of the hybridization bond and/or the ability of the hybridized probe to be detected. In part, these improvements include the replacement of certain base pairs with analogs or the modification of the probe to incorporate certain detection compounds.

In certain situations, it might be desired to replace some of the bases within the probe with non-base analogs. For example, the base adenine may be replaced with diaminopurine. This modification would result in a stronger bond between the probe and any homologous DNA present in a sample.

To facilitate detection of hybridized probe, various chemical modifications to the DNA sequence are possible. One example of these modifications includes sulfonating the DNA. Sulfonated DNA allows for increased detectability in reaction such as ELISA methods. In addition, through biotinylation, or the use of a biotin analog of a particular base, it is possible to incorporate a biotin site into the probe. The incorporation of a biotin site would facilitate detection of the hybridized probe in an avidin-biotin system.

Further, radiolabels may be incorporated into the probes for use and detection in labs. At the present, 32 is preferred for use as a labeling method.

Various methods may be used with these probes to detect the presence of *Listeria monocytogenes* in a sample. These include radioimmunoassays (RIA); enzyme-linked immunosorbent assays (ELISA) and other types of diagnostic, qualitative assays commonly known to those of ordinary skill in the art.

EXAMPLE 1—Creation of pCL102

Identification of a DNA region encoding listeriolysin O.

Chromosamal DNA of hemolytic *L. monocytogenes* strain L028 digested with MboI had been cloned in the BamHI site of the cosmid vector pHC79. After transformation in *E. coli* HB101, several hemolytic clones were obtained, identified as ampicillin resistant colonies producing a halo of lysis on ampicillin blood agar plates. Spontaneous deletion of the original clones led to a stable derivative pCL101. Two deletions were created on the cosmid pCL101 between identical restriction sites (BamHI and SalI) to give pCL102 which contained an insert of 8.5 kilobases of *L. monocytogenes* DNA. Its restriction map is shown on FIG. 1. The hemolytic activity transformed in the extracts of *E. coli* monocytogenes strain HB101 was detected as described by Boyer in J. Mol. Biol. 41:459–464 (1969) The activity of transformants harboring pCL101 or pCL102 (7.5 HU/ml of overnight culture) is lower than that measured in the *Listeria* supernatants (64 HU/ml of overnight culture). By Western blot analysis of the extracts, using an antiserum against listeriolysin O a protein of the same molecular weight as the listeriolysin O (60-kilodaltons) was detected.

Antilisteriolysin O serum preparation

Female albino rabbits were immunized by repeated subcutaneous inoculations of highly purified hemolysin from *L. monocytogens*. The protocol was based on 3 injections of 75 g of toxin in complete Freund's adjuvant and one injection of the same dose in incomplete Freund's adjuvant. Blood was harvested 2 weeks after the last injection.

Western blot analysis

For Western blot analysis, protein were electrophoretically transferred to nitrocellulose sheets in a Trans-Blot cell apparatus with blotting buffer containing 20% (v/v) methanol. The sheets were incubated for 1 h at room temperature with shaking in 50 mM Tris, 150 mM NaCl solution (pH 8.0) and 5% (w/v) skim milk prior to 1 h incubation in anti-listeriolysine O immune serum diluted (1:20) in the above buffer. The sheets were washed eight times in buffer before addition of 20 ml of milk buffer containing 0.01 $\mu$Ci (0.37 kBq) of $^{125}$I-protein A. Shaking was continued for a further 1 h and then the filters were washed six times in Duffer supplemented with 0.1% Triton X-100. The filters were dried at 80° C. and then autoradiographed using Kodak X-O-mat SO-282) film.

EXAMPLE 2—Localization of hylA in pCL102

Localization of hylA in pCL102 was achieved by using 400-base-pair DNA probe carrying part of the listeriolysin O gene called hylA and part of Tn1545: a 410-base-pair HindIII fragment of pCL102 hybridized to the probe (FIG. 1). It revealed the presence of a stop codon, presumably the end of the hylA gene.

Nucleotide sequence determination

The dideoxy chain terminator sequencing method was used with the modification of Biggin et al. The technique which generates sequential deletions of the insert starting at the cloning site using T4 polymerase was used as described by IBI.

Nucleotide sequence of hylA.

Figure 2B:
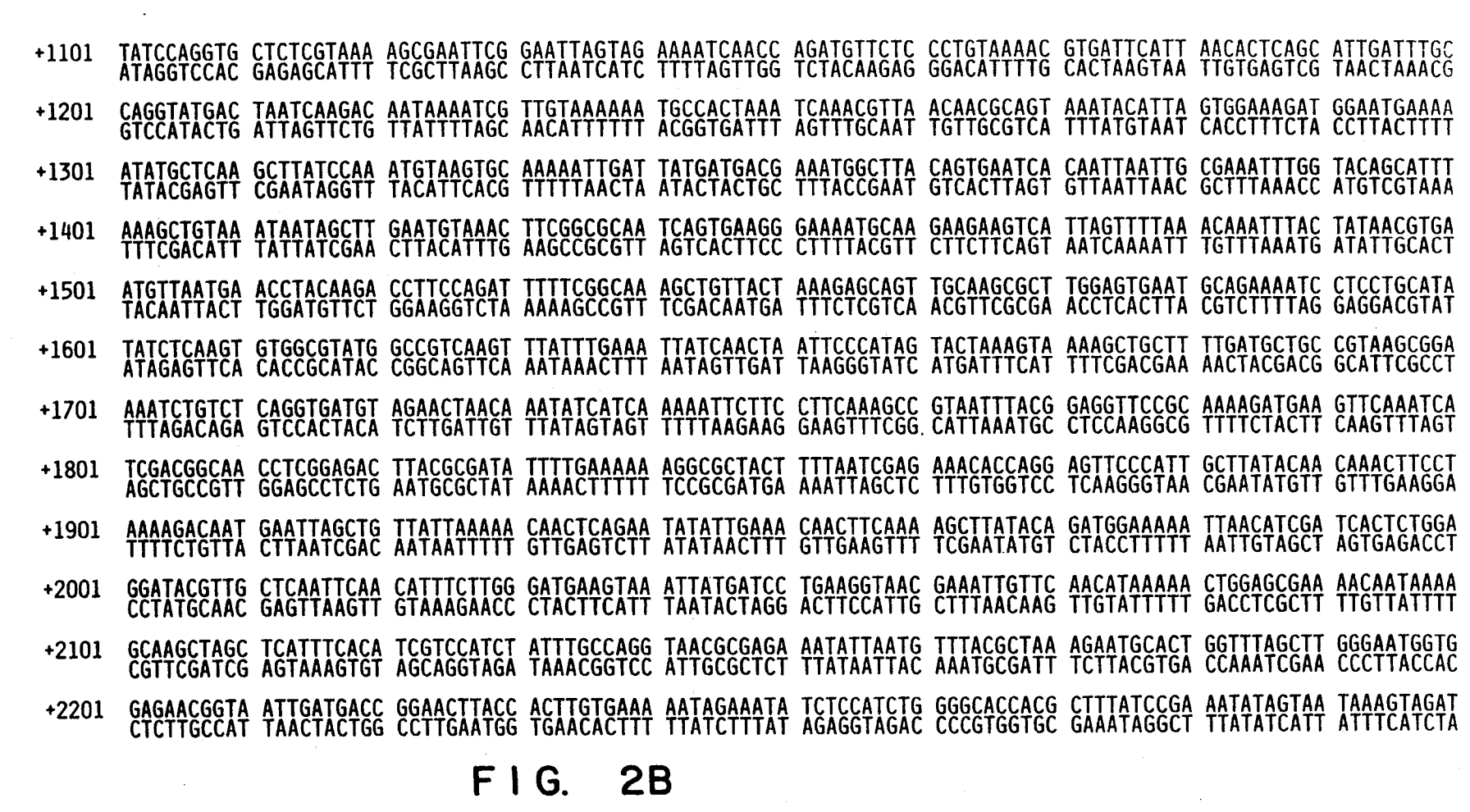

The nucleotide sequence of hylA and its upstream region is indicated on FIG. 2. The open reading frame which ends in the 410-base-pair HindIII fragment (see below) starts in the 1670-base-pair HindIII fragment and is 1617-base-pair long. The first ATG in the sequence is located 30 nucleotides downstream from the beginning of this ORF. It is preceded 10 nucleotides upstream by an hexanucleotide (AAGGAG) complementary to the 3' end of the 16 S RNA of *L. monocytogenes*. If this ATG is considered as the start codon of hylA, the gene is 36% GC rich, a value which is in agreement with that calculated for *L. monocytogenes* (36–38%). This value is higher than that of the sequences adjacent to the gene.

We looked for the presence of gram positive promoter-like sequences: upstream from the ORF, two TA-TAAT sequences are detected but these sequences are not preceded by a "−35" close to the Consensus TTGACA. The hemolysin production known to be regulated by factors such as iron was examined for sequences similar to the consensus identified as target for iron binding regulatory proteins but none was detected. The exact location of the prometer is under study.

The codon usage in hylA is reported in Table 3 where we also report the average codon usage in six other genes from gram positive bacteria, i.e. *Streptococcus* and *Staphylococcus* and in 25 highly expressed genes of *E. coli*. Codons ending by an A or a T are more widely used (72%) in hylA than in *E. coli* genes (44%). This is in agreement with the different GC% of these different organisms. In addition, in most of the cases, the codons rarely used in hylA are rarely used in genes of gram positive bacteria. Codons which are rarely used in *E. coli* genes but which are used in staphylococcal or streptococcal genes are also used in hylA. As already proposed, this probably reflects differences in the distribution of tRNAs between bacteria of different GC content and is probably a genome strategy to modulate gene expressivity.

Analysis of the deduced protein sequence

The gene hylA encodes for a protein of 529 amino-acids, which corresponds to a protein of 58.6 kDa. The amino-terminal sequence presents all the characteristics of signal sequences of gram positive bacteria: the first residues are hydrophilic and positively charged. They are followed by about twenty hydrophobic residues. The putative cleavage site of the signal peptidase lies probably after lysine 25 as the sequence starting at residue 26 is highly homologous to the amino-terminal sequence of the SH-dependant hemolysin secreted by *Listaria ivanovii*. The signal sequence of listeriolysin O has a length comparable to the average length of signal sequences of gram positive bacteria genes. Consequently, the secreted listeriolysin O (without the signal sequence) contains 504 amino-acids and has a molecular mass of 55.8 kDa. This value is in agreement with the molecular weight of the protein purified from *L. monocytogenes* culture supernatants.

The amino-acid composition of the protein does not reveal any special feature except the presence of a unique cysteine: this residue is located in the carboxy-terminal part of the sequence, in position 484. It is known that listeriolysin O, like all cytotoxins of the streptolysin O family, is thiol-activable. Reagents which block the SH-group inhibit the activity of this toxin, and in particular, inhibit the binding to cholesterol which is thought to be the first step in the cytolytic activity of this protein. Thus the carboxy-terminal region containing the unique cysteine is probably essential for activity. Two lines of evidence are in favor of this statement. (i) In the Hly-mutant, the transposon had inserted in codon 481 of hylA, three codons upstream from the cysteine codon, giving rise to a truncated protein devoid of hemolytic activity. (ii) Comparison of listerielysin O with two other SH-dependent hemolysins, streptolysins, streptolysin O and pneumolysin reveals the presence of a conserved undecapeptide containing the unique cysteine, in the three proteins (see next Example).

EXAMPLE3—Comparison of listeriolysin O with streptolysin O and pneumolysin

It is well known that SH-activated hemolysins immunologically cross-react. It has been recently shown that streptolysin O from *Streptococcus pyogenes* and pneumolysin from *Streptococcus pneumoniae* share homologies. These proteins have identical molecular weight, if one takes into account the secreted form of streptolysin O, the pneumolysin being a non secreted protein. When one aligns the sequences at the unique cysteine present in the carboxy-terminal end of these proteins, the highest homology lies in the region of this unique cysteine. We compared the amino-acid sequence of listeriolysin O (LLO) to the sequences of streptolysin O (SLO) and pneumolysin (PLY). These three proteins have similar sizes. The secreted forms of LLO and SLO are respectively 504 and 471 amino-acids long, pneumolysin is 471 amino-acids long. The putative signal sequence of LLO (25 aminoacids) is shorter than that of SLO (33 amino-acids). The three sequences can be completely aligned at the unique cysteine, if one introduces two deletions of one amino-acid for SLO and one deletion of one amino-acid for PLY. This alignment reveals strong homologies: the percentage of amino-acid identity between two sequences compared two by two in the common 469 residue region, is about 42–43%. Interestingly, the signal sequence of listeriolysin O corresponds to the N-terminal part of streptolysin O, the hydrophobic amino-acids of listeriolysin O being changed for hydrophilic ones. This region is the region of lowest homology. Homolgies between the three proteins are evident along the whole sequence but they are stronger towards the carboxy-terminal end. In particular, around the unique cysteine, an eleven-amino-acid peptide is conserved in the three sequences. If one compares the sequences in terms of similarity (and not identity), one observes even stronger homologies, illustrated by the superimposition of the hydrophobicity profiles.

At the DNA level, the genes do not show substantial homology (between 52% to 54% homologies when comparing any two of the three genes). Nevertheless, in the region coding for the conserved undecapeptide, the homology at the DNA level is 73% between ply and hylA, 88% between slo and hylA and 82% between slo and ply. These results are in agreement with previous results: when, using a DNA fragment internal to slo as a probe, the homologies between *S. pyogenes* and *L. monocytogenes* could not be detected. Indeed, the probe used did not correspond to the region of highest homology and the conditions used could only detect 80% homology. It is highly probable that use of a probe corresponding to the nucleotide sequence coding for the common eleven-amino-acid region would have led to different results.

EXAMPLE 4—Detection of hlyA in the different species of the genus Listeria

As listeriolysin O is now considered as a major virulence factor, it seemed interesting to test if hylA was present in the different species of the genus Listeria. By Southern blot analysis, we looked for the presence of hylA in several *Listeria monocytogenes* strains and in the other species of the genus, i.e. *L. ivanovii, L. seeligeri, L. innocua, L. welshimeri, L. murrayi*. We used, as a probe, a DNA fragment internal to the gene: the 651-base-pair HindII fragment which extends from codon to codon. The results, with the probe used, were unambiguous, even at low stringencies. The gene hylA is only detected in *L. monocytogenes*, even in the strains which are non-hemolytic such as the type strain ATCC15313 and Audurier 86/776.

What is claimed is:

1. A method for the detection of *Listeria monocytogenes* in a sample, wherein said method comprises:
    (a) placing the sample in a media capable of supporting growth of bacteria of the genus Listeria;
    (b) disrupting any bacterial cells present in the sample to release bacterial DNA;
    (c) additionally treating said disrupted sample to denature the bacterial DNA;
    (d) contacting said denatured bacterial DNA with an oligonucleotide under hybridization conditions whereby said oligonucleotide can hybridize to denatured *L. monocytogenes* DNA;
    (e) detecting any hybridized oligonucleotide; and
    (f) correlating presence of hybridized oligonucleotide with the presence of *L. monocytogenes*; and
further wherein said oligonucleotide is one strand of a HindIII restriction fragment of the sequence:

```
5'-AA GCTTATCCAA ATGTAAGTGC
3'-TT CGAATAGGTT TACATTCACG

AAAAATTGAT TATGATGACG AAATGGCTTA
TTTTTAACTA ATACTACTGC TTTACCGAAT

CAGTGAATCA CAATTAATTG CGAAATTTGG
GTCACTTAGT GTTAATTAAC GCTTTAAACC

TACAGCATTT AAAGCTGTAA ATAATAGCTT
ATGTCGTAAA TTTCGACATT TATTATCGAA

GAATGTAAAC TTCGGCGCAA TCAGTGAAGG
CTTACATTTG AAGCCGCGTT AGTCACTTCC

GAAAATGCAA GAAGAAGTCA TTAGTTTTAA
CTTTTACGTT CTTCTTCAGT AATCAAAATT

ACAAATTTAC TATAACGTGA ATGTTAATGA
TGTTTAAATG ATATTGCACT ACAATTACT

ACCTACAAGA CCTTCCAGAT TTTTCGGCAA
TGGATGTTCT GGAAGGTCTA AAAAGCCGTT

AGCTGTTACT AAAGAGCAGT TGCAAGCGCT
TCGACAATGA TTTCTCGTCA ACGTTCGCGA

TGGAGTGAAT GCAGAAAATC CTCCTGCATA
ACCTCACTTA CGTCTTTTAG GAGGACGTAT
```

-continued

```
CTTCAAAGCC GTAATTTACG GAGGTTCCGC
GAAGTTTCGG CATTAAATGC CTCCAAGGCG

AAAAGATGAA GTTCAAATCA TCGACGGCAA
TTTTCTACTT CAAGTTTAGT AGCTGCCGTT

CCTCGGAGAC TTACGCGATA TTTTGAAAAA
GGAGCCTCTG AATGCGCTAT AAAACTTTTT

AGGCGCTACT TTTAATCGAG AAACACCAGG
TCCGCGATGA AAATTAGCTC TTTGTGGTCC

AGTTCCCATT GCTTATACAA CAAACTTCCT
TCAAGGGTAA CGAATATGTT GTTTGAAGGA

AAAAGACAAT GAATTAGCTG TTATTAAAAA
TTTTCTGTTA CTTAATCGAC AATAATTTTT

CAACTCAGAA TATATTGAAA CAACTTCAAA
GTTGAGTCTT ATATAACTTT GTTGAAGTTT

AGCTT-3'
TCGAA-5'.
```

2. A composition comprising a labelled oligonucleotide of hlyA, wherein said oligonucleotide is one strand of a HindIII restriction fragment of the sequence:

```
5'-AA GCTTATCCAA ATGTAAGTGC AAAAATTGAT TATGATGACG AAATGGCTTA
3'-TT CGAATAGGTT TACATTCACG TTTTTAACTA ATACTACTGC TTTACCGAAT

CAGTGAATCA CAATTAATTG CGAAATTTGG TACAGCATTT AAAGCTGTAA ATAATAGCTT
GTCACTTAGT GTTAATTAAC GCTTTAAACC ATGTCGTAAA TTTCGACATT TATTATCGAA

GAATGTAAAC TTCGGCGCAA TCAGTGAAGG GAAAATGCAA GAAGAAGTCA TTAGTTTTAA
CTTACATTTG AAGCCGCGTT AGTCACTTCC CTTTTACGTT CTTCTTCAGT AATCAAAATT

ACAAATTTAC TATAACGTGA ATGTTAATGA ACCTACAAGA CCTTCCAGAT TTTTCGGCAA
TGTTTAAATG ATATTGCACT ACAATTACT TGGATGTTCT GGAAGGTCTA AAAAGCCGTT

AGCTGTTACT AAAGAGCAGT TGCAAGCGCT TGGAGTGAAT GCAGAAAATC CTCCTGCATA
TCGACAATGA TTTCTCGTCA ACGTTCGCGA ACCTCACTTA CGTCTTTTAG GAGGACGTAT

TATCTCAAGT GTGGCGTATG GCCGTCAAGT TTATTTGAAA TTATCAACTA ATTCCCATAG
ATAGAGTTCA CACCGCATAC CGGCAGTTCA AATAAACTTT AATAGTTGAT TAAGGGTATC

TACTAAAGTA AAAGCTGCTT TTGATGCTGC CGTAAGCGGA AAATCTGTCT CAGGTGATGT
ATGATTTCAT TTTCGACGAA AACTACGACG GCATTCGCCT TTTAGACAGA GTCCACTACA

AGAACTAACA AATATCATCA AAAATTCTTC CTTCAAAGCC GTAATTTACG GAGGTTCCGC
TCTTGATTGT TTATAGTAGT TTTTAAGAAG GAAGTTTCGG CATTAAATGC CTCCAAGGCG

AAAAGATGAA GTTCAAATCA TCGACGGCAA CCTCGGAGAC TTACGCGATA TTTTGAAAAA
TTTTCTACTT CAAGTTTAGT AGCTGCCGTT GGAGCCTCTG AATGCGCTAT AAAACTTTTT

AGGCGCTACT TTTAATCGAG AAACACCAGG AGTTCCCATT GCTTATACAA CAAACTTCCT
TCCGCGATGA AAATTAGCTC TTTGTGGTCC TCAAGGGTAA CGAATATGTT GTTTGAAGGA

AAAAGACAAT GAATTAGCTG TTATTAAAAA CAACTCAGAA TATATTGAAA CAACTTCAAA
TTTTCTGTTA CTTAATCGAC AATAATTTTT GTTGAGTCTT ATATAACTTT GTTGAAGTTT

AGCTT-3'
TCGAA-5'.
```

```
TATCTCAAGT GTGGCGTATG GCCGTCAAGT
ATAGAGTTCA CACCGCATAC CGGCAGTTCA

TTATTTGAAA TTATCAACTA ATTCCCATAG
AATAAACTTT AATAGTTGAT TAAGGGTATC

TACTAAAGTA AAAGCTGCTT TTGATGCTGC
ATGATTTCAT TTTCGACGAA AACTACGACG

CGTAAGCGGA AAATCTGTCT CAGGTGATGT
GCATTCGCCT TTTAGACAGA GTCCACTACA

AGAACTAACA AATATCATCA AAAATTCTTC
TCTTGATTGT TTATAGTAGT TTTTAAGAAG
```

3. A composition comprising a labelled oligonucleotide of hlyA, wherein said oligonucleotide is a nucleic acid selected from the group consisting of:
   a) 5'-TTCCGCAAAAGATGAAGTTCAAAT-CATCGAC-3';
   b) 5'-TAATAGCTTGAATG-TAAACTTCGGCGCAAT-3';
   c) 5'-ATCAACTAATTCCCATAGTACTA-3'; and
   d) 5'-ACCTCGGAGACTTACG-CGATATTTTG-3';

or a nucleic acid fully complementary to said nucleic acid.

4. The composition comprising a labelled oligonucleotide as claimed in claim 3, wherein the oligonucleotide is 5'-TTCCGCAAAAGATGAAGTTCAAATCATCGAC-3'.

5. The composition comprising a labelled oligonucleotide as claimed in claim 3, wherein the oligonucleotide is 5'-TAATAGCTTGAATGTAAACTTCGGCGCAAT-3'.

6. The composition comprising a labelled oligonucleotide as claimed in claim 3, wherein the oligonucleotide is 5'-ATCAACTAATTCCCATAGTACTA-3'.

7. The composition comprising a labelled oligonucleotide as claimed in claim 3, wherein the oligonucleotide is 5'-ACCTCGGAGACTTACGCATATTTTG-3'.

8. A method for the detection of *L. monocytogenes* in a sample, wherein said method comprises:
   (a) placing the sample in a media capable of supporting growth of bacteria of the genus Listeria;
   (b) disrupting any bacterial cells in the sample to release bacterial DNA;
   (c) additionally treating said disrupted sample to denature the bacterial DNA;
   (d) contacting said denatured bacterial DNA with an oligonucleotide under hybridization conditions whereby said oligonucleotide can hybridize to denatured *L. monocytogenes* DNA;
   (e) detecting any hybridized oligonucleotide; and
   (f) correlatinq the presence of hybridized oligonucleotide with the presence of *L. monocytogenes;* and further wherein said oligonucleotide is a nucleic acid selected from the group consisting of
   1) 5'-TTCCGCAAAAGATGAAGTTCAAATCATCGAC-3';
   2) 5'-TAATAGCTTGAATGTAAACTTCGGCGCAAT-3';
   3) 5'-ATCAACTAATTCCCATAGTACTA-3'; and
   4) 5'-ACCTCGGAGACTTACGCGATATTTTG-3'
or a complementary nucleic acid fully complementary to said nucleic acid.

9. The method for detection of *L. monocytogenes* as claimed in claim 8, wherein said oligonucleotide is 5'-TTCCGCAAAAGATGAAGTTCAAATCATCGAC-3'.

10. The method for detection of *L. monocytogenes* as claimed in claim 8, wherein said oligonucleotide is 5'-TAATAGCTTGAATGTAAACTTCGGCGCAAT-3'.

11. The method for detection of *L. monocytogenes* as claimed in claim 8, wherein said oligonucleotide is 5'-ATCAACTAATTCCCATAGTACTA-3'.

12. The method for detection of *L. monocytogenes* as claimed in claim 8, wherein said oligonucleotide is 5'-ACCTCGGAGACTTACGCGATATTTTG-3'.

* * * * *